(12) United States Patent
Zhao

(10) Patent No.: US 11,111,512 B2
(45) Date of Patent: Sep. 7, 2021

(54) METHOD FOR PRODUCING 5-HYDROXYTRYPTOPHAN

(71) Applicants: BLRH BIOTECH CO., Baoding (CN); NANJING SHOUBAI BIOTECH CO., Nanjing (CN)

(72) Inventor: Yunxian Zhao, Baoding (CN)

(73) Assignees: BLRH BIOTECH CO., Baoding (CN); NANJING SHOUBAI BIOTECH CO., Nanjing (CN)

( * ) Notice: Subject to any disclaimer, the term of this patent is extended or adjusted under 35 U.S.C. 154(b) by 0 days.

(21) Appl. No.: 16/311,381

(22) PCT Filed: Jun. 5, 2017

(86) PCT No.: PCT/CN2017/091859
§ 371 (c)(1),
(2) Date: Dec. 19, 2018

(87) PCT Pub. No.: WO2019/006701
PCT Pub. Date: Jan. 10, 2019

(65) Prior Publication Data
US 2020/0199635 A1    Jun. 25, 2020

(51) Int. Cl.
*C12P 13/22*    (2006.01)
*C12N 1/20*    (2006.01)
*C12R 1/10*    (2006.01)

(52) U.S. Cl.
CPC .............. *C12P 13/227* (2013.01); *C12N 1/20* (2013.01); *C12N 1/205* (2021.05); *C12R 2001/10* (2021.05)

(58) Field of Classification Search
CPC ........... C12P 13/227; C12P 13/22; C12P 7/08; C12N 1/20; C12N 1/205; C12R 1/10; C12R 2001/10
See application file for complete search history.

(56) References Cited

U.S. PATENT DOCUMENTS

| 3,830,696 A | 8/1974 | Daum et al. |
| 9,663,768 B2 * | 5/2017 | Yan .................... C12P 13/04 |
| 2016/0060638 A1 | 3/2016 | Yan et al. |

FOREIGN PATENT DOCUMENTS

| CN | 105385646 A | 3/2016 |
| WO | 2015175793 A1 | 11/2015 |

OTHER PUBLICATIONS

Zhuang et al., Biotechnology and Bioprocess Engineering, 2012, vol. 17, p. 1041-1047.*
International Search Report and Written Opinion from corresponding PCT Patent Application No. PCT/CN2017/091859 in Chinese.

* cited by examiner

*Primary Examiner* — Kade Ariani
(74) *Attorney, Agent, or Firm* — Grogan, Tuccillo & Vanderleeden, LLP

(57) ABSTRACT

This invention involves to *Bacillus licheniformis* JSC-69 for producing the 5-HTP, deposited as CGMCC NO: 13533; and a method for the producing 5-HTP using *Bacillus licheniformis*. *Bacillus licheniformis* JSC-69 said in this invention produces 5-HTP using tryptophan as the substrate, and the transformation efficiency is 95%~100%.

8 Claims, No Drawings

METHOD FOR PRODUCING 5-HYDROXYTRYPTOPHAN

CROSS REFERENCE TO RELATED APPLICATION

This application is a national stage patent application of International Application No. PCT/CN2017/091859 filed on Jul. 5, 2017, which is incorporated herein in its entirety.

TECHNICAL FIELD

This invention involves a *bacillus* and a fermentation method for producing 5-hydroxytryptophan with this *bacillus*, which falls into the field of biotechnology.

BACKGROUND TECHNOLOGIES 5-hydroxytryptophan (5-HTP) is a precursor of human hormone serotonin with sedative effect and can help the body produce this hormone to maintain a balance. 5-HTP is a reaction medium for tryptophan and serotonin (a compound amine), in another word, 5-HTP is an important precursor for inhibitory neurotransmitter compound amine (5-HT). Complex amine is present in the brain, platelets, intestine, stomach and central nervous system. When the mood changes, compound amine is correspondingly secreted; it is an important chemical substance for the brain to control emotion, behavior, appetite, sleep and impulse. Since 5-HTP can effectively help produce compound amine, it is able to promote emotional and nervous health. Studies have shown that 5-HTP can suppress appetite, reduce fat intake, alleviate anxiety, control mood, and promote sleep. Currently, domestic company U-Seed Biotech Inc. stably produces this product, and its product quality has been approved by European and American countries.

5-HTP as a food ingredient is naturally extracted from the seeds of Griffonia simplicifolia, a medicinal plant grown in West African. 5-HTP is an acidic substance of natural amino acid and can be found in many dietary proteins. 5-HTP is a natural substitute for prescription drug Prozac. Like Prozac, 5-HTP can enhance serotonin activity.

Serotonin, a hormone secreted in the brain, can affect the mood, sleep and appetite. In the case of serotonin imbalance in the brain, 5-HTP is needed to maintain the body in a normal state. Therefore, when the content is too low, it can easily cause depression, anxiety and sleep disorder. Drugs such as Prozac can prevent brain cells from depleting serotonin too quickly to result in serotonin deficiency. However, the efficacy of 5-HTP is slightly different: It increases the production level of serotonin in brain cells to increase the content.

5-HTP can produce serotonin in human body and help with the important substance in normal nerves and brain functions. Serotonin can help sleep and effectively control pain. Accordingly, 5-HTP is successfully used to treat sleep disorders. Because serotonin is the predecessor of melatonin (a natural hormone regulating sleep-wake cycle), melatonin content increases as serotonin level elevates. Since 5-HTP and SSRI have similar actions, why not use the latter? The first reason is that prescription antidepressants are expensive; the second reason is that the prescription drug can often cause some untoward side effects, including dry mouth, anxiety and loss of libido.

In addition, by suppressing appetite, 5-HTP makes the body ingest less carbohydrates and sense satiety more quickly. Daily intake of 750mg 5-HTP can reduce the absorption of carbohydrates without increasing body weight so that weight loss can be achieved.

Clinical application of 5-HTP: 1. Antidepressant and sedative: 5-HTP increases the production of serotonin in brain cells and further increases serotonin content. 5-HTP produces serotonin in human body, which can help with neurologically important normal substance and brain functions. Serotonin can help with sleep, effectively control pain and treat depression; 2. Alleviating stress and improving sleep: When serotonin level elevates, melatonin content also increases, resulting in better sleep; 3. Weight loss: It can effectively control appetite, increase the sensitivity of satiety center, and reduce the sense of hunger in diet control of weight loss process, making weight loss easier to accomplish. It is currently a popular supplement for diet food. It is a great news for people who want to lose weight; 4. Other: In addition to the traditional medicinal and anti-depressive function, it is also effective on weight loss, drug rehabilitation, improving sleep, relieving premenstrual syndrome, migraine headaches, etc.; currently, 5-HTP is widely used by major health product companies in Europe and America. It is used to increase the production of compound amines in human blood by naturally increasing the level of serotonin. Currently, 5-HTP is mainly prepared from plant sources and is extracted from Griffonia seed in Africa. However, the production is limited by resource availability and the extraction cost is high. Obviously, microbial transformation and fermentation is a more desirable production method.

CONTENT OF THIS INVENTION

In order to address the existing technical issues, the purpose of this invention is to provide a *bacillus* and a fermentation method for the production of 5-HTP with this *bacillus*.

A novel strain *Bacillus licheniformis* for producing 5-HTP, namely *Bacillus licheniformis* JSC-69 was deposited Jan. 5, 2017 at the China General Microbiological Culture Collection Center (CGMCC) and given accession number CGMCC NO: 13533.

Identification of the said *Bacillus licheniformis* JSC-69:
1. Morphological characteristics of this *bacillus:* Individual *bacillus* should be 0.6×2.0 μm, this Gram-positive and aerobic bacterium is able to move without capsule or chain. The elliptical or cylindrical spore is 0.9×1.5 μm sitting in the middle or at one end with enlarged middle portion. When cultured on a broth agar plate, the colonies are approximately round, milky white, dark surface and opaque with irregular edge; the colonies are rough, adhering and expanding. The colonies adhere to the culture medium and are difficult to pick. In liquid culture, it has membrane without turbidity or precipitation.
2. Physiological and biochemical identification of the *bacillus:* When the physiological and biochemical properties of *Bacillus licheniformis* JSC-69 are determined, the results should show that: This strain is catalase test positive. Gelatine liquefication, amylolysis and V.P test should also be positive, with citrate utilization. The methyl red test and lecithinase test are negative; it is able to utilize nitrate, but it is also able to utilize D-glucose, L-arabinose, D-xylose and D-mannitol to produce acid.

This invention further provides a method for producing 5-HTP using the said *Bacillus licheniformis* JSC-69 as described in the application, and this method specifically includes the following steps:

1. Step a, culturing the *Bacillus licheniformis* JSC-69;
2. Step b, transforming of tryptophan with the procuct produced from the step a;
3. Step c, collecting the 5-HTP.

Further, the "culturing" described in Step a should comprise any one or a combination of slant culturing, shake flask culturing, seed tank culturing and fermenter culturing.

The medium used for culturing step is an aqueous medium containing absorbable carbon, nitrogen and phosphorus sources. The medium may also include suitable salts, minerals, metals and other nutrients; the carbon source is selected from one or more of glucose, fructose, sucrose, galactose, dextrin, glycerin, starch, syrup and molasses; the nitrogen source is selected from one or more of ammonium chloride, ammonium sulfate, ammonium nitrate, and potassium nitrate.

Wherein, the medium used in shake flask and seed tank culturing is an aqueous medium containing absorbable carbon, nitrogen and phosphorus sources; the medium may also include suitable salts, minerals, metals and other nutrients; the carbon source is selected from one or more of glucose, fructose, sucrose, galactose, dextrin, glycerin, starch, syrup, and molasses; the nitrogen source is selected from one or more of ammonium chloride, ammonium sulfate, ammonium nitrate, and potassium nitrate. The components of optimized culture medium include tryptone, soy peptone, beef extract, yeast extract, glucose, corn syrup and sodium chloride.

The medium used in fermenter culturing is an aqueous medium containing absorbable carbon, nitrogen and phosphorus sources. The medium may also include suitable salts, minerals, metals, and other nutrients; the carbon source is selected from one or more of glucose, fructose, sucrose, galactose, dextrin, glycerin, starch, syrup, and molasses; the nitrogen source is selected from one or more of ammonium chloride, ammonium sulfate, ammonium nitrate, and potassium nitrate. The components of optimized medium include: sucrose, bean pulp, $(NH_4)_2SO_4$, $K_2HPO_4 \cdot 3H_2O$, $KH_2PO_4$; the composition of further optimized medium includes: 40 g/L sucrose, 40 g/L bean pulp, 5 g/L $(NH_4)_2SO_4$, 8 g/L $K_2HPO_4 \cdot 3H_2O$ and 1.8 g/L $KH_2PO_4$; the initial pH is 6.5~7.0.

Further, the conditions of culturing described in Step a are: temperature is 25-45° C., pH is 6.5-7.0, and time is 20-50 h.

Wherein, shaking flask and seed tank culturing conditions are: 25-45° C.; pH 6.5-7.0, for 20-30 h.

The fermenter culturing conditions are: fermentation temperature is 30-35° C.; pH is 6.5-7.0, and fermentation time is 30-50h. The optimized fermentation temperature is 32° C.; pH is 6.8, and fermentation time is 45 h.

Further, tryptophan concentration described in Step b is 0.2-10 g/L; the transforming condition is: transforming under 25-45° C.;and pH 6-8 for 40-60 h.

Further, "Collecting the 5-HTP" described in Step c includes the following method: centrifuging the transformed product obtained in Step b and collecting the supernatant, which is the product 5-HTP.

Further, the methods of this invention also include Step d, that is purifying the product 5-HTP. The "purifying" process includes solid-liquid separation, cation exchange resin adsorption separation, concentration, ethanol dissolution and distillation steps in order of sequence.

"Culturing" described in this invention aims to amplify the strain, during which a certain quantity and quality of strains are eventually obtained after activating the dormant strain, followed by stepwise expanded culturing. The general process of the said "culturing" includes: slant culture, shake flask culture, seed tank stepwise culture and fermenter culture. In actual practice, the seed tank culture passages can be determined according to fermentation scale, bacterial growth characteristics, inoculum size and related factors.

"Substrate" described in this invention refers to the reactants to be transformed; "transforming" refers to the process in which the reactants are transformed into desired products under suitable conditions through specific metabolic pathways using the microbes. This invention uses "tryptophan" as substrate to produce the final product "5-HTP" through transformation with the help of a specific strain *Bacillus licheniformis* JSC-69.

When compared with general *Bacillus*, *Bacillus licheniformis* JSC-69 said in this invention has a wider range of fermentation temperature (30~37° C.) can use compound nitrogen sources, grow quickly to achieve higher biomass in a short period of time, and biotransform tryptophan to produce 5-HTP. By optimizing the fermentation conditions, *Bacillus licheniformis* JSC-69 produces 5-HTP using tryptophan as the substrate, and the transformation efficacy is 95%~100%. The transformation medium can be further purified to obtain high-purity 5-HTP.

EXPERIMENTAL EXAMPLES

Examples 1

Screening of Bacterial Strains

Plate screening medium: 5 g/L beef extract, 10 g/L soy peptone, 5 g/L NaCl, and 15 g/L agar. Liquid screening medium: 20 g/L sucrose, 20 g/L bean pulp, 3 g/L $(NH_4)_2SO_4$, 5 g/L $K_2HPO_4 \cdot 3H_2O$, 1 g/L $KH_2PO_4$, 2 g/L beef extract, 4 g/L soy peptone, 5 g/L NaCl, 8 g/L tryptophan; pH is 7.0.

More than 100 soil or water samples were collected from Nanjing and surrounding areas to prepare appropriate concentrations of dilutions, the prepared samples are directly applied to screening medium plates, cultured at 37° C. for 1 day. Then, single colony of different morphologies are selected and inoculated into test tubes containing liquid medium. After shake culture at 30° C. and 200rpm for 2 days, fermentation supernatant is centrifuged. The 5-HTP content in the supernatant sis determined. 5-HTP production is detected in 4 of more than 500 colonies.

The strains obtained after initial screening are separately inoculated into test tubes containing 5ml liquid medium and shake-cultured at 30° C. for 2 days. It is then transferred into a flask containing 50ml liquid medium and fermented at 30° C. 200rpm for 2 days. The content of 5-HTP in fermentation supernatant is accurately determined using HPLC. See Table 1 for results.

TABLE 1

| 5-HTP production status of screened strains | |
|---|---|
| Strain No. | 5-HTP content (g/L) |
| JSC-24 | 1.2 |
| JSC-69 | 7.7 |
| JSC-137 | 6.8 |
| JSC-403 | 0.4 |

The results show that 5-HTP content in JSC-69 and JSC-137 fermentation broth is significantly higher than in the fermentation broth of the other two strains.

Examples 2

Identification of Strain JSC-69

The morphological, physiological and biochemical characteristics of JSC-69 are determined according to "Bergey's Manual of Determinative Bacteriology" (2nd Edition 2, 2004). After streak culture on plate medium for 1 day, the colonies are characterized by approximately round shape, milky white color, dark surface, opaque, irregular edge, coarse, sticky and spreading appearance. The colonies tightly adhere to the culture medium and are difficult to pick; in liquid culture, it has membrane without turbidity or precipitation. Individual *bacillus* should be 0.6×2.0 μm, this Gram-positive and aerobic bacterium is able to move without capsule or chain. The elliptical or cylindrical spore is 0.9×1.5 μm sitting in the middle or at one end with enlarged middle portion. The physiological and biochemical properties JSC-69 are determined, the results should be: the results show that this strain is catalase test positive. Gelatine liquefication, amylolysis and V.P test should also be positive, with citrate utilization. The methyl red test and lecithinase test are negative; it is able to utilize nitrate, but it is also able to utilize D-glucose, L-arabinose, D-xylose and D-mannitol to produce acid.

Based on the analysis of morphological, physiological and biochemical characteristics, JSC-69 is considered to be a new strain of *Bacillus licheniformis* and named as *Bacillus licheniformis* JSC-69. This strain was deposited at China General Microbiological Culture Collection Center, the number is CGMCC NO: 13533.

Examples 3

Fermentation Culturing of Strain JSC-69 and Producing the Target Product

1. Culturing
(1) Primary seed culture: Monoclonal strains that have been freshly cultured in plate seed culture medium for ~18 h are inoculated into 6 ml of liquid seed culture medium and cultured at 37° C. 225 rpm for ~24 h. Plate seed medium composition (/L): 5 g beef extract, 10 g soy peptone, 5 g NaCl, 1 L water and 15 g agar. Liquid seed medium composition (/L): 5 g beef extract, 10 g soy peptone, 5 g NaCl and 1 L water, pH is7.0. Sterilization is carried out under 0.1 MPa for 20 min.
(2) Secondary seed culture: 6ml of the primary seed culture medium is inoculated into a 1000 ml shake flask containing 200 ml of secondary seed culture medium and cultured at 30° C., 225 rpm for ~24 h. OD600 is 6.0-10. Secondary seed culture medium composition is: 0.1% peptone, 0.2% corn syrup, 0.5% glucose and 0.5% yeast extract, pH is 8.0.
(3) Culture in fermentation tank
   1) Fermentation medium composition: See Table 2. Initial pH is 6.5~7.0.

TABLE 2

| Composition of fermentation medium | |
| --- | --- |
| Name | Use amount (g/L) |
| Sucrose | 40 |
| Bean pulp | 40 |
| (NH$_4$)$_2$SO$_4$ | 5 |

TABLE 2-continued

| Composition of fermentation medium | |
| --- | --- |
| Name | Use amount (g/L) |
| K$_2$HPO$_4$·3H$_2$O | 8 |
| KH$_2$PO$_4$ | 1.8 |

2) Primary technical parameters and optimization and screening Basic technical parameters: Inoculum size is 1%; fermentation temperature is 31° C., pH is 6.7; and fermentation time is 40 h.

Based on these basic technical parameters, shake flask test is carried out; inoculum size, fermentation temperature, pH, fermentation time and other factors are optimized and screened. Shake flask test method: The strain is inoculated into a test tube containing 5 ml of seed medium to shake-culture at 30° C. for 2 days. It is then transferred into a shake flask containing 50 ml of fermentation medium, in which 8 g/L tryptophan substrate is added. The content of 5-HTP in fermenting supernatant is accurately determined with HPLC.

a) Effect of Inoculum Size

The effects of different inoculum sizes on catalytic synthesis of 5-HTP are examined. Other technical parameters: fermentation temperature is 31° C., pH is 6.7; and fermentation time is 40 h. See Table 3 for results.

TABLE 3

| Effect of different inoculum size on 5-HTP catalytic synthesis | |
| --- | --- |
| Inoculums size (%) | 5-HTP content (g/L) |
| 0.5 | 7.3 |
| 1.0 | 7.8 |
| 1.5 | 7.7 |
| 2.0 | 7.6 |

It can be seen in Table 3 that too low (0.5%) or too high (2.0%) the inoculum size has adverse effect on catalyzed synthesis of 5-HTP with tryptophan, and 1.0% inoculum size is preferred. It is possible that low inoculum size affects bacterial growth; when the inoculum size is too high, rapid bacterial growth facilitates aging to further affect catalytic efficacy.

b) Effect of Fermentation Temperature

The effects of different fermentation temperatures on catalytic synthesis of 5-HTP are investigated. Other technical parameter conditions: inoculum size is 1.0%; pH is 6.7; and fermentation time is 40h. The results are shown in Table 4.

TABLE 4

| Effect of different fermentation temperature on 5-HTP catalytic synthesis | |
| --- | --- |
| Fermentation temperature (° C.) | 5-HTP content (g/L) |
| 30 | 7.6 |
| 31 | 7.7 |
| 32 | 7.8 |
| 33 | 7.6 |
| 34 | 7.4 |
| 35 | 7.3 |

It can be seen in Table 4 that the fermentation temperature has a certain effect on catalytic synthesis of 5-HTP with tryptophan. The catalytic effect is poorer below 32° C. than at 32° C.; and the efficacy becomes poorer with higher temperature. The optimal fermentation is observed at 32° C.

c) Effects of pH

The effects of different pH on catalytic synthesis of 5-HTP are examined. Other technical parameter conditions: inoculum size is 1.0%; fermentation temperature is 32° C., and fermentation time is 40 h. See Table 5 for results.

TABLE 5

Effect of different pH on 5-HTP catalytic synthesis

| pH | 5-HTP content (g/L) |
|---|---|
| 6.5 | 7.2 |
| 6.6 | 7.3 |
| 6.7 | 7.7 |
| 6.8 | 7.9 |
| 6.9 | 7.7 |
| 7.0 | 7.3 |

It can be seen in Table 5 that pH has a certain effect on catalytic synthesis of 5-HTP with tryptophan. The catalytic efficacy is poorer below or above pH 6.8 than at pH 6.8. The optimal catalytic efficacy is observed at pH 6.8.

d) Effect of Fermentation Time

The effect of different fermentation times on catalytic synthesis of 5-HTP are examined. Other technical parameter conditions: inoculum size is 1.0%; fermentation temperature is 32° C., pH is 6.8. See Table 6 for results.

TABLE 6

Effect of different fermentation time on 5-HTP catalytic synthesis

| Fermentation time (h) | 5-HTP content (g/L) |
|---|---|
| 30 | 6.7 |
| 35 | 7.0 |
| 40 | 7.8 |
| 45 | 7.9 |
| 50 | 7.8 |
| 55 | 7.8 |

It can be seen in Table 6 that there are certain differences in the catalytic synthesis of 5-HTP with tryptophan under different fermentation times, and the catalytic efficacy gradually increases with longer fermentation time. However, the catalytic efficacy peaks in 45 h without subsequent increase. Therefore, the optimal fermentation time is 45 h.

Therefore, the optimized technical parameters after optimization and screening: inoculum size is 1%; fermentation temperature is 32° C., pH is 6.8; and fermentation time is 45 h.

3) Process and Procedures

1. Seed preparation requirements: Strain identification conforms to its properties without variations or other bacteria.
2. Medium preparation: The ingredients are accurately weighed according to the formula. Sucrose is fully dissolved with appropriate amount of water; (NH4)2SO4, K2HPO4.3H2O and KH2PO4 are fully dissolved with appropriate amount of water. The amount of defoaming agent should be appropriate.
3. Sterilization of empty fermentation tank: Temperature is 121~130° C. with circulating steam, tank pressure is 0.09~0.15 Mpa, and the maintenance time is 30 min.
4. Feeding materials and adding water: The total volume is adjusted.
5. Sterilization of filled fermentation tank: Temperature is 121° C. tank pressure 0.08~0.15Mpa, ventilation volume is 0.8~1.0 vvm, the maintenance time is 30 min with circulating steam; the temperature is finally cooled down to 30° C.
6. Inoculation: inoculum size is 1%.
7. Culture: The temperature is 32° C., the time is 45 h, the tank pressure is 0.05~0.08 Mpa, pH is 6.8, DO is 25% or higher. Spore formation rate is 98%; when the culture is terminated, the bacterial suspension for JSC-69 transformation is obtained; bacteria density is ≥2.0× $10^9$ cfu/ml. It should cool down and maintain the pressure.

2. Transformation and Production of Target Product (1) Collecting the bacterial cells: The product produced from culturing *Bacillus licheniformis* JSC-69 for transforming is centrifuged at 4000 r/min for 10 min to collect bacterial cell sediment.

(2) Transforming: 0.2M phosphate buffer (pH 7.4) is added to the bacterial cell sediment to form a bacterial density of $3.0×10^7$~$8.0×10^7$/ml; then, 8.0 g/L tryptophan is added to carry out transformation for 45 h at 32° C., 1.0 L/min, and 225 r/min.

Preparation of 0.2M phosphate buffer (pH 7.4): 71.6 g Na2HPO4.12H2O is dissolved in 1000 ml water to obtain 0.2M Na2HPO4; then 31.2 g NaH2PO4.2H2O is dissolved in 1000ml water to obtain 0.2M NaH2PO4; finally, 19ml of 0.2M NaH2PO4 and 81ml of 0.2M Na2HPO4 are evenly mixed.

(3) Solid-liquid separation: The transformation liquid is centrifuged at 4000r/min for 10min to obtain 5-HTP-containing supernatant. *Bacillus licheniformis* JSC-69 produces 5-HTP using tryptophan as the substrate, and the 24 h transformation rate is 95%~100%.

Example 4

Purification and Extraction of the Product

1. Solid-liquid separation of fermentation broth: Bacterial cells are collected using centrifugation or ceramic membrane separation method.
2. The 001×7 cation-exchange resin (732) is used for adsorption and separation, followed by elution with ammonia water.

Based on screening, 001×7 cation-exchange resin results in the best adsorption separation efficiency, suitable for large-scale production of 99% specifications of 5-HTP. The adsorption separation conditions of 001×7 resin are as follows: At room temperature, 5-HTP mass concentration of the loading solution is 10.8 mg/ml, pH is adjusted to 3.5, and the sample is loaded at 4.0 ml/min, 7.0% ammonia water with a volume 3 times the resin is used for elution at 3.0 ml/min. 5-HTP mass fraction is >99.0% and the ash content is <1.0% after concentration and crystallization of the eluate.

3. Concentrating Into Solid S5tate

Double-effect or multi-effect evaporation of the eluate is carried out to concentrate into solid, followed by drying to remove the moisture.

4. Hot water dissolution, high-selectivity resin adsorption and separation.

The concentrated solid is dissolved in hot water, followed by further high-selectivity resin adsorption and separation of 5-HTP to remove impurities. After elution with aqueous ammonia, it is concentrated and crystallized to obtain high-purity 5-HTP.

Examples 5

Product Analysis Method

Product analysis method employs HPLC. The standard solutions and samples of tryptophan and 5-HTP are chromatographically determined with a Shimadzu C18 reverse-phase column, using 0.05% trichloroacetic acid (TCA)-methanol (68.75:31.25, v/v) as the mobile phase. Injection volume: 10 μL, mobile phase flow rate: 1.5 ml/min gradient elution, the wavelength of UV spectrophotometric detector is 275 nm. All solutions are filtered through a 0.45 μm filter before use. External standard method is used for calculation.

The invention claimed is:

1. A method for producing 5-HTP, by Bacillus licheniformis JSC-69 deposited under accession number CGMCC 13533, said method comprising the following steps:
   Step a) culturing of Bacillus licheniformis said Bacillus licheniformis JSC-69;
   Step b) adding tryptophan to said culture of step a) and transforming the tryptophan to 5-HTP by said Bacillus licheniformis JSC-69;
   Step c) collecting the 5-HTP.

2. The method of claim 1, wherein the culturing step comprising any one or a combination of slant culturing, shake flask culturing, seed tank culturing and fermenter culturing.

3. The method of claim 2, wherein the fermenter culturing is carried out under 30-35° C. and pH 6.5-7.0 for 30-50 h.

4. The method of claim 2, wherein the medium of fermenter culturing comprises sucrose, bean pulp, $(NH_4)_2SO_4$, $K_2HPO_4 \cdot 3H_2O$ and $KH_2PO_4$.

5. The method of claim 1, wherein the tryptophan concentration in Step b is 0.2-10 g/L.

6. The method of claim 1, wherein the transforming in Step b is carried out under 25-45° C. and pH 6-8 for 40-60 h.

7. The method of claim 1, wherein the collecting described in Step c includes the following method: centrifuging the transformed product obtained in Step b and collecting the supernatant, which is the product 5-HTP.

8. The method of claim 1, further comprising Step d, that is purifying the product 5-HTP, the "purifying" process includes solid-liquid separation, cation exchange resin adsorption separation, concentration, ethanol dissolution and distillation steps in order of sequence.

* * * * *